United States Patent [19]

Pierce

[11] Patent Number: 5,893,878
[45] Date of Patent: Apr. 13, 1999

[54] MICRO TRAUMATIC TISSUE MANIPULATOR APPARATUS

[76] Inventor: Javin Pierce, 4780 Mountain Rd., Stowe, Vt. 05672

[21] Appl. No.: 08/842,335

[22] Filed: Apr. 24, 1997

[51] Int. Cl.⁶ ................................................ A61B 17/28
[52] U.S. Cl. .................. 606/207; 606/205; 606/207; 606/208; 606/264; 600/152; 600/153; 600/154; 600/155
[58] Field of Search ........................... 606/207, 205, 606/208; 600/564, 152, 153, 154, 155, 652, 653, 654, 655

[56] References Cited

U.S. PATENT DOCUMENTS

| | | |
|---|---|---|
| 3,895,636 | 7/1975 | Schmidt . |
| 4,619,260 | 10/1986 | Magill et al. . |
| 4,955,897 | 9/1990 | Ship ................................. 606/207 |
| 5,275,615 | 1/1994 | Rose . |
| 5,290,309 | 3/1994 | Kothe . |
| 5,565,004 | 10/1996 | Christoudias . |
| 5,569,274 | 10/1996 | Rapacki et al. .................... 606/158 |
| 5,638,606 | 6/1997 | Marlow ............................. 606/207 |
| 5,667,526 | 9/1997 | Levin ................................ 606/207 |
| 5,693,069 | 12/1997 | Shallman .......................... 606/207 |

FOREIGN PATENT DOCUMENTS

| | | | |
|---|---|---|---|
| 0 380 874 | 8/1990 | European Pat. Off. . | |
| 164403 | 11/1963 | U.S.S.R. ............................. | 606/207 |
| 1161094 | 6/1985 | U.S.S.R. . | |
| WO 95/07662 | 3/1995 | WIPO . | |

*Primary Examiner*—Michael Buiz
*Assistant Examiner*—Vy Quang Bui
*Attorney, Agent, or Firm*—Snell & Wilmer, .L.L.P.

[57] ABSTRACT

An apparatus for surgically manipulating tissue without causing irreparable damage to the tissue during retention and manipulation is disclosed. The tissue manipulator apparatus includes a shaft having proximal and distal ends, a rod member with proximal and distal ends circumferentially contained within the shaft, a contact member having at least one tissue contact surface area comprising a plurality of projections connected to the distal end of the rod member, and a handle member attached near the proximal end of the shaft. The plurality of projections preferably point in the direction of retraction of the targeted tissue. The apparatus is designed to distribute the interdentating contact over the tissue micro surface area in an effort to reduce reliance on pressure induced friction alone.

16 Claims, 8 Drawing Sheets

MICRO TRAUMATIC TISSUE MANIPULATOR APPARATUS

BACKGROUND OF THE INVENTION

1. Field of the Invention

The present invention relates generally to a device for surgically manipulating tissue without damaging the tissue. More particularly, the present invention relates to a tissue manipulating instrument having at least one of sharp extensions, barbs, teeth, serrations, or similar structures of sufficient length to penetrate a tissue surface and having a geometry that resists further incision of tissue whereby torque can be exerted by the distribution of the extensions, barbs, teeth or serrations.

2. Description of Related Art

Several tools have been developed for manipulating tissue by friction, trauma, such as hooking and puncturing, and a combination of friction and trauma which include coacting jaws such as those that are present in forceps and tweezers. The two most common classification for surgical graspers are traumatic and atraumatic.

A traumatic surgical grasper typically has at least one tissue penetrating element on one jaw and often has two coacting or interdentating teeth on the other which function to provide holding power via shear forces that are applied to the hole that is created by penetrating the tissue. For example, U.S. Pat. No. 4,619,260 issued to Magill et al. discloses a tissue-retrieving means for a surgical instrument having a snare loop projecting outwardly for encircling projecting body tissue and means for contracting the loop to sever the encircled tissue. The retrieving means includes tissue engaging means and manipulating means. The tissue engaging means preferably comprises means for impaling the encircled tissue including a barb movable between a contracted position for inserting the barb into the encircled tissue and an expanded position assumed upon the removal of the tissue on the engaging means.

Although effective for certain tissue manipulations, a traumatic surgical grasper is capable of producing undesirable effects. For example, in laproscopic cholecystectomy where prehension of the gall bladder is desired, a traumatic grasper would perforate or tear the gall bladder thereby releasing septic bile into the peritoneal cavity thus causing the patient great danger. Therefore, many instances of tissue manipulation require means for manipulating the tissue without affecting the structural integrity of the tissue.

An atraumatic grasper functions by compressing tissue against jaws that are typically covered with serrated, roughened, or ridged surfaces which are capable of creating friction but are not sharp enough to make incisions into the tissue. One example of such an atraumatic tissue grasper is shown in U.S. Pat. No. 5,275,615 issued to Rose. The Rose patent discloses a forceps type medical instrument with tissue gripping jaws. The jaw arrangement includes a pair of members having opposing wavy and serrated surfaces which open and close against one another to enable tissue to be retained therein by means of friction.

Another atraumatic tissue grasper is shown in U.S. Pat. No. 5,565,004 issued to Christoudias. This patent reference describes a twin forceps approximator having two movable plates joined together at one end and a central plate having the same length which is joined to the two plates at the one end. The two movable plates close against opposite sides of the central plate either simultaneously or sequentially. Teeth are located on the inside surface of the free ends of the plates or jaws in order to engage the tissue between the jaws so that the tissue can be rotated or manipulated.

Many types of tissue forceps exist in the medical instrument art which comprise the basic design of two mobile plates joined at one end. The inside surfaces of these plates often comprise complimentary teeth or ridges which function to hold the tissue between the flexible plates. The size of the plates or jaws, the configuration of the contact surface, and the presence or absence of teeth on the plates or jaws are the characteristics used to categorize and identify the various forceps by name. Most of these tissue forceps are also considered to be atraumatic tissue graspers.

Like traumatic tissue graspers, atraumatic tissue graspers may also produce undesirable effects. More specifically, with respect to the same example used in association with the traumatic tissue grasper, namely laproscopic cholecystectomy, sufficient atraumatic grasper prehension force can create a point load on the gall bladder that can perforate it, or an over pressure to the ligated sac that can induce failure or extravasation.

The present invention overcomes the shortcomings associated with the above described traumatic and atraumatic tissue graspers by distributing the minimally penetrating contact over the tissue micro surface. This provides substantial holding power over the contact surface with less reliance on pressure induced friction. Although the surface of the tissue undergoes multiple incisions by the mechanism of prehension with the present invention, the incisions are of insufficient size to effect the structural integrity of the organ. The present invention also overcomes similar limitations associated with surgical tissue manipulation in general where tissue is simply too slippery to hold or retain easily such as is the case with arthroscopic manipulation of cartilage.

SUMMARY OF THE INVENTION

It is a principal object of the present invention to provide a tissue manipulator which can retain and manipulate tissue without causing irreparable damage to the tissue during retention and/or manipulation.

It is another object of the present invention to provide a tissue manipulator which distributes minimally penetrating or micro traumatic contact with the tissue over the tissue micro surface area.

It is still another object of the present invention to provide a tissue manipulator which does not rely on pressure induced friction alone to retain the tissue.

It is yet another object of the present invention to provide a micro traumatic tissue manipulator that comprises a plurality of projections of sufficient length and geometry to minimally penetrate a substantial area of tissue surface to enable the retention and manipulation of the tissue without effecting the structural integrity of the structure associated with the tissue.

In brief, the present invention is directed to a tissue manipulator which includes an elongated shaft, a contact member having at least one tissue contact surface that comprises a plurality of serrations, teeth, stipples, barbs, hooks or other type projections in close approximation with one another over the entire surface area of the contact surface that minimally puncture the tissue surface, and a handle member attached to an end of the shaft to control the contact member. The handle member can control the release or retention of the tissue within the contact member. The projections are preferably configured to point in the desired direction of traction or retrograde of the tissue. The contact member preferably comprises a set of co-acting jaws. The contact member and handle member may be removable and replaceable.

The present invention is also directed to a method of tissue prehension which includes the steps of puncturing the tissue surface with a plurality of pointed projections, maintaining a minimal amount of pressure against the projections to maintain contact between the tissue and the projections, and imparting a torque to the tissue to effect the retention of the tissue on the projections and to move the tissue to the desired location. The plurality of pointed projections are preferably configured in close approximation to one another and cover enough of the tissue surface area so as to minimize the pressure induced friction required to maintain contact between the projections and the tissue.

These and other objects, features, and advantages of the present invention will become more apparent to those skilled in the art from the following more detailed description of the preferred embodiments taken with reference to the accompanying drawings.

DETAILED DESCRIPTION OF THE PREFERRED EMBODIMENTS

Figure 1:
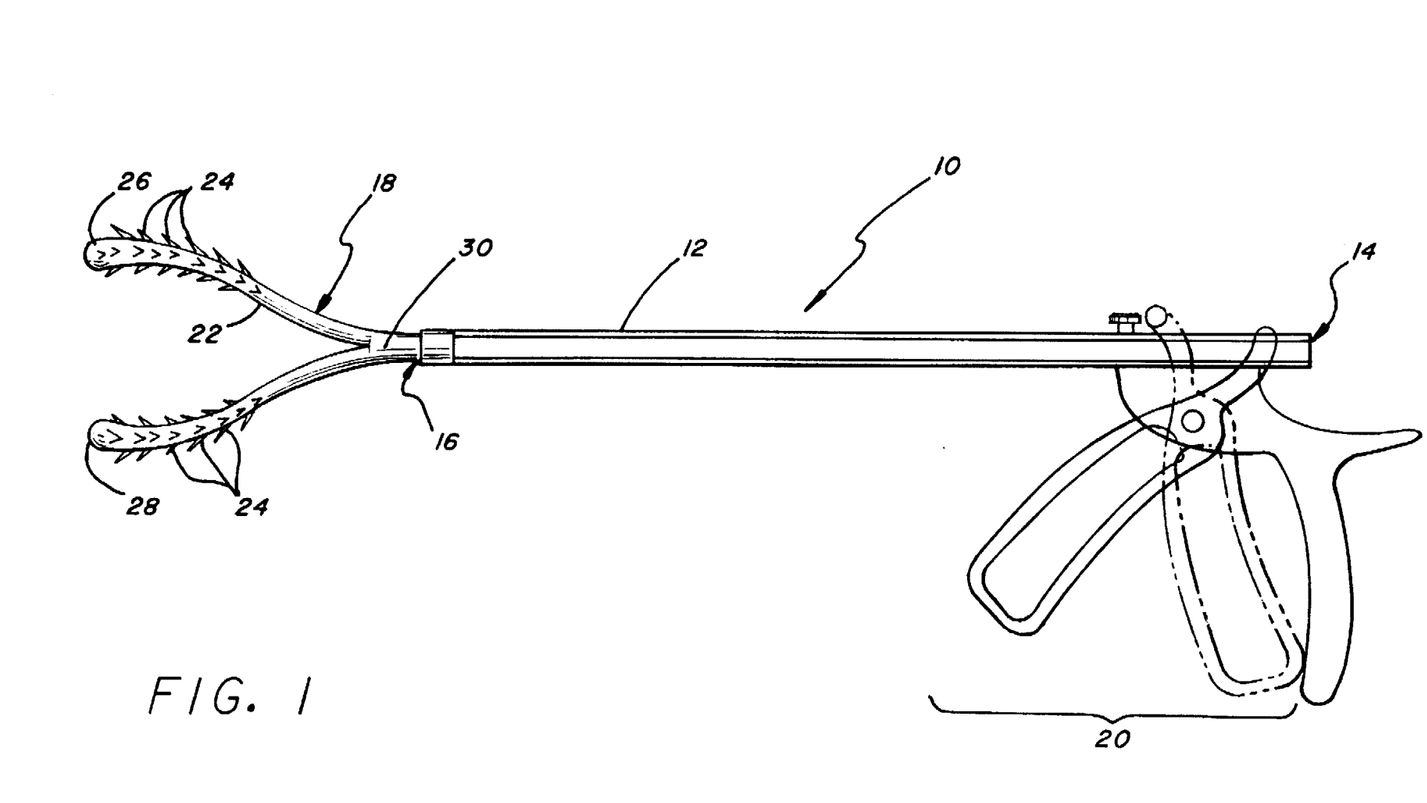
FIG. 1 is a side elevational view of the micro traumatic tissue manipulator apparatus of the present invention shown with the contact member fully extended from the shaft.

Referring now to the figures, where numerals represent various parts of the present invention, a side elevational view of the micro traumatic tissue manipulator apparatus 10 of the present invention is shown in FIG. 1. The apparatus 10 comprises an elongated hollow shaft 12 having proximal and distal ends 14 and 16, a contact member 18 attached near the distal end 16 of the shaft 12, and a handle member 20 attached near the proximal end 14 of the shaft 12. The contact member 18 includes at least one tissue contact surface 22 which comprises a plurality of peaked or pointed projections 24. The projections 24 preferably protrude from the tissue contact surface 22 in a direction of traction or retrograde of the targeted tissue. The contact member 18 is retracted within the shaft 12 in order to manipulate and adjust the tissue contact surface 22 in relation to the targeted tissue. The contact member 18 may take the form of a conventional single action grasper or a double action grasper comprising a set of co-acting jaw members 26 and 28 as shown in FIG. 1. The jaw members 26 and 28 are preferably comprised of a flexible metal and are connected to one another at their like ends 30. Alternatively, the contact member may take the form of a pad which can have a variety of shapes, including circular and elliptical, having a plurality of projections extending from its tissue contact surface or a simple rod member or stick having a plurality of projections extending from its tissue contact surface(s). This type of contact member configuration would be particularly useful for positioning a flat piece of tissue onto a surface such as in articular cartilage repair.

Figure 2:
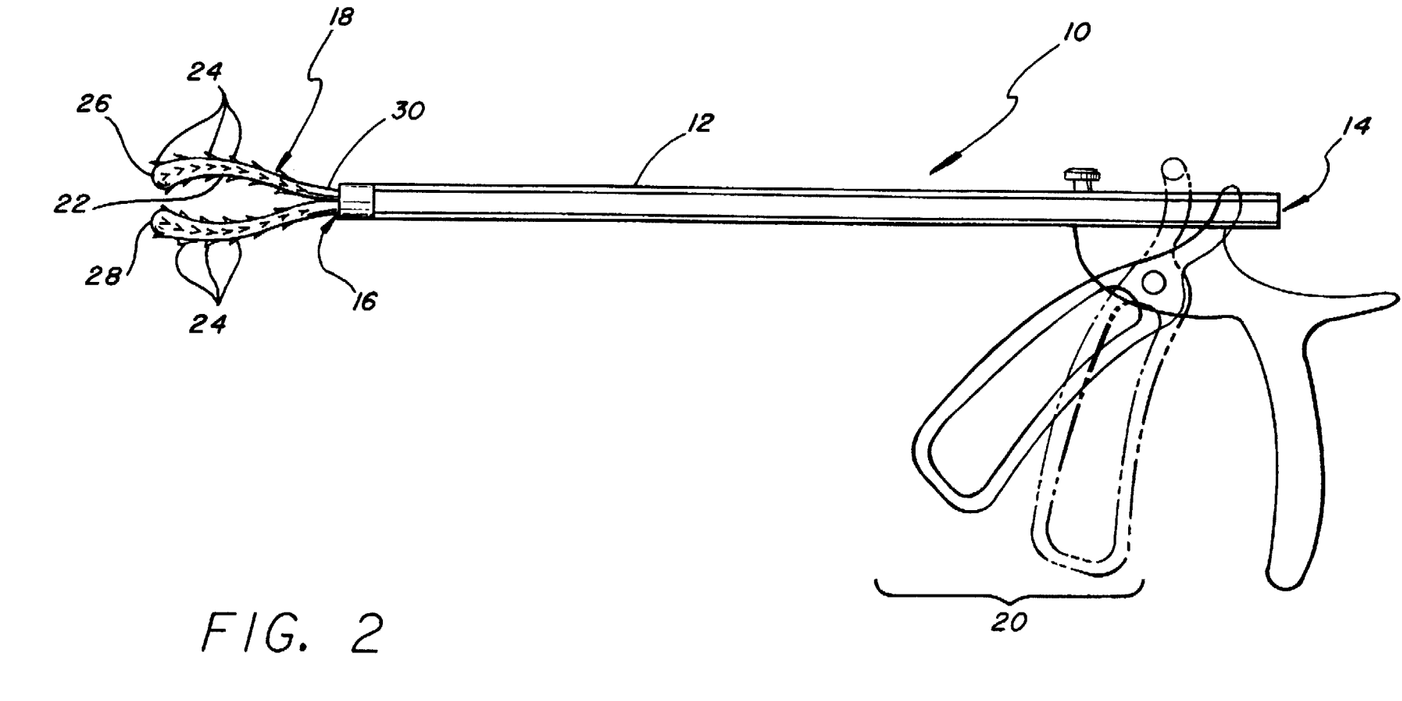
FIG. 2 is a side elevational view of the micro traumatic tissue manipulator apparatus of the present invention shown with the contact member partially retracted within the sheath.
Figure 3:
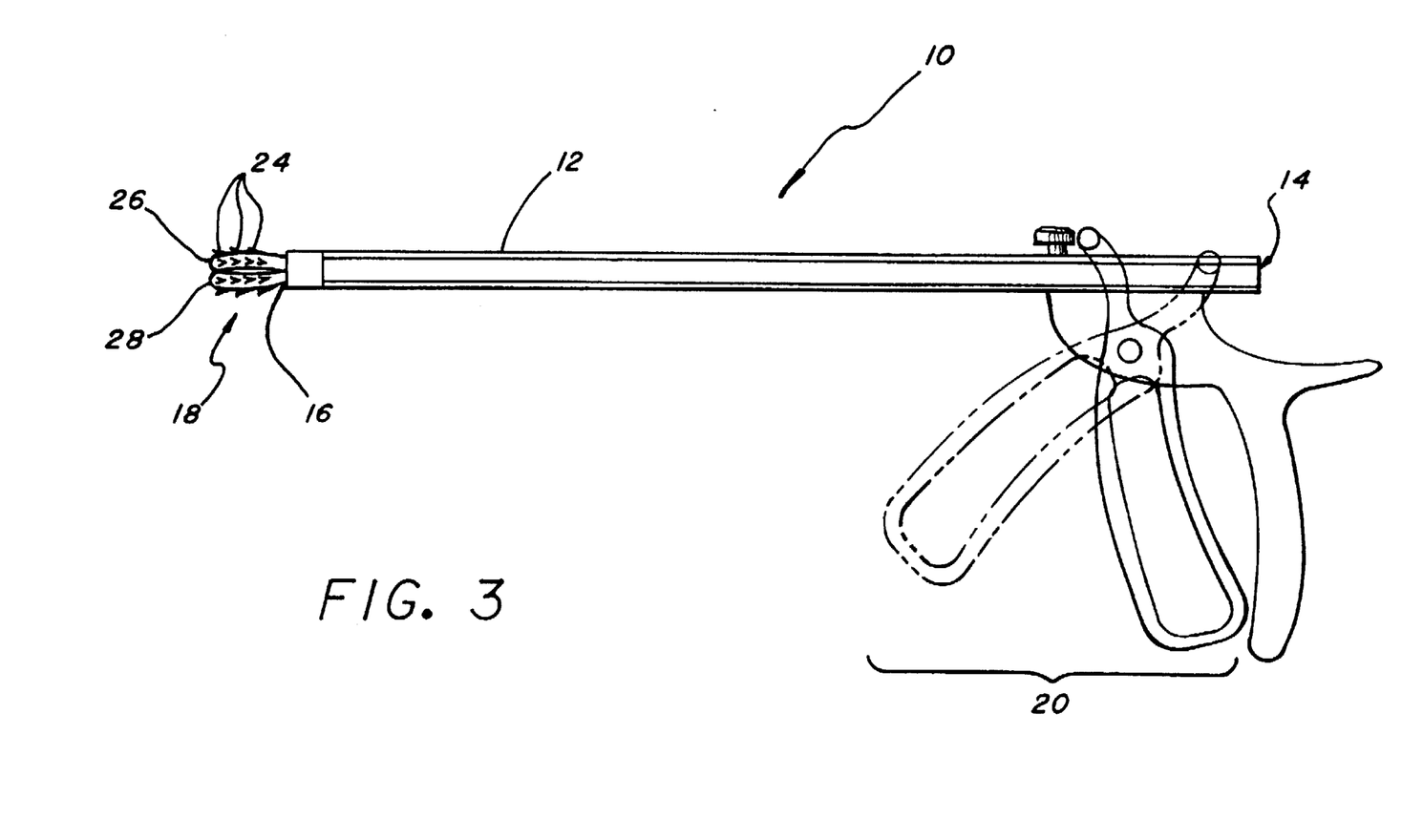
FIG. 3 is a side elevational view of the micro traumatic tissue manipulator apparatus of the present invention shown almost entirely retracted within the shaft.

FIG. 2 illustrates another side elevational view of the tissue manipulator apparatus 10 shown in FIG. 1 with the contact member 18 shown partially retracted within the shaft 12. The handle member 20 is employed to retract the contact member 18 within the shaft 12 thereby enabling the targeted tissue to be retained between the jaw members 26 and 28 of the contact member 18. Means for retracting the contact member 18 within the shaft 12 using the handle member 20 is described in further detail with reference to FIGS. 4 and 5. FIG. 3 illustrates yet another side elevational view of the tissue manipulator apparatus 10 shown in FIGS. 1 and 2 with the contact member 18 shown almost entirely retracted within the shaft 12.

Figure 4:
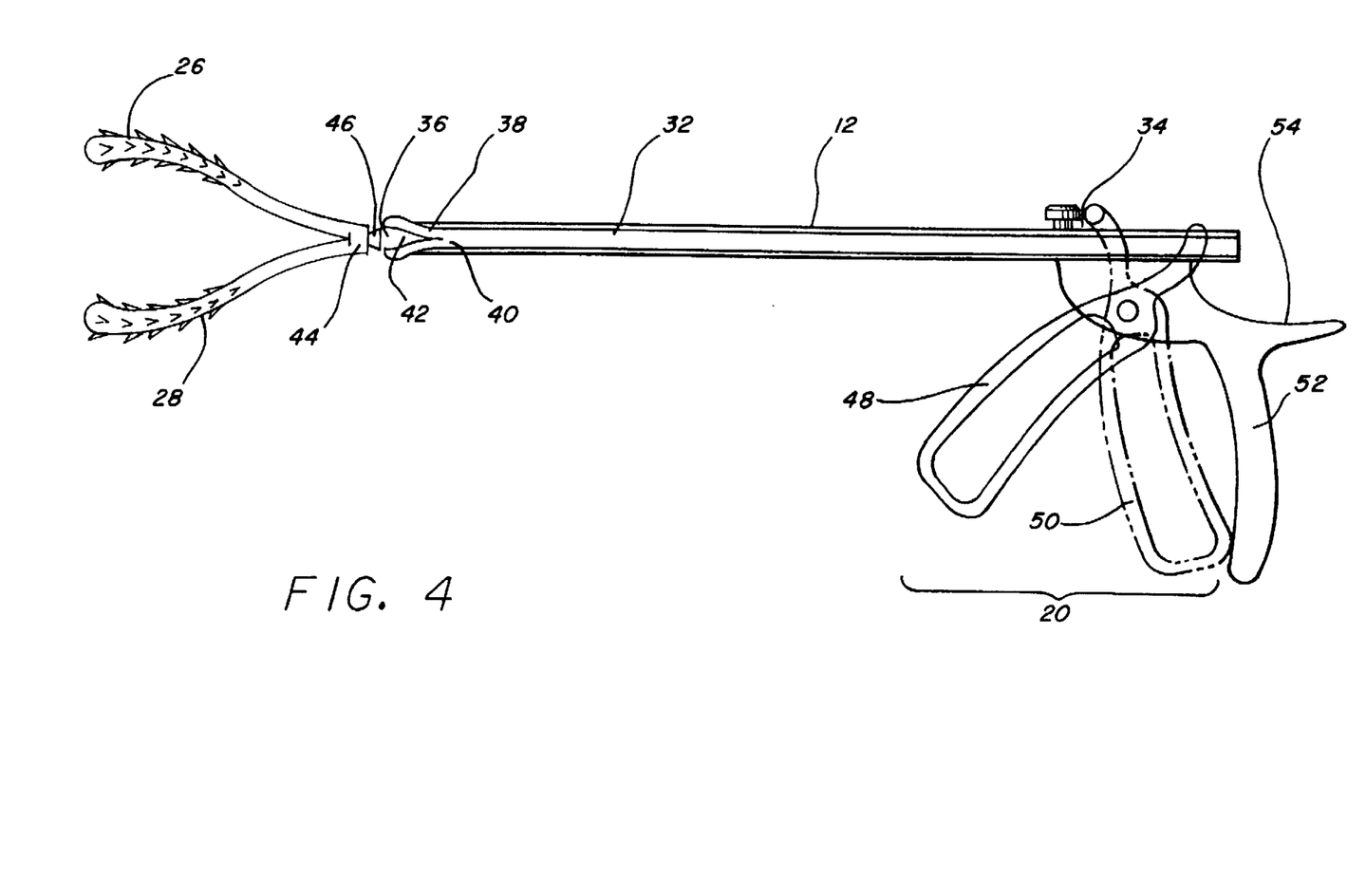
FIG. 4 is a longitudinal cross-sectional view of FIG. 1 with the contact member shown detached.

Turning now to FIG. 4, a longitudinal cross-sectional view of FIG. 1 is depicted with the contact member 18 shown detached. FIG. 4 illustrates that the manipulator apparatus 10 further comprises a rod member 32 having a proximal end 34 and a distal end 36 wherein the rod member 32 is circumferentially contained within the shaft 12. The distal end 36 of the rod member 32 comprises attachment means in the form of an axially split tube having upper and lower members 38 and 40 separated by an opening 42. The end 44 of the contact member 18 where the jaw members 26 and 28 are connected terminates in a protuberance 46 which is capable of being secured within the opening 42 via a snap-type fit. Other attachment means for connecting the end 44 of the contact member 18 to the distal end 36 of the rod member 32 are also contemplated by the present invention and may include, but are not limited to, a screw type mechanism, a spring loaded mechanism, and a removable pin which traverses both the diameter of the rod 32 and the diameter of the protuberance 46 or contact member 18.

The handle member 20 comprises movable first and second handle levers 48 and 50 and stationary member 52 having a thumb stop 54. The first and second handle levers 48 and 50 are attached to each other and the stationary member 52 via a spring type mechanism or pivoting means. The functioning of the handle member 20 is shown and explained in greater detail with reference to FIG. 5.

Figure 5:
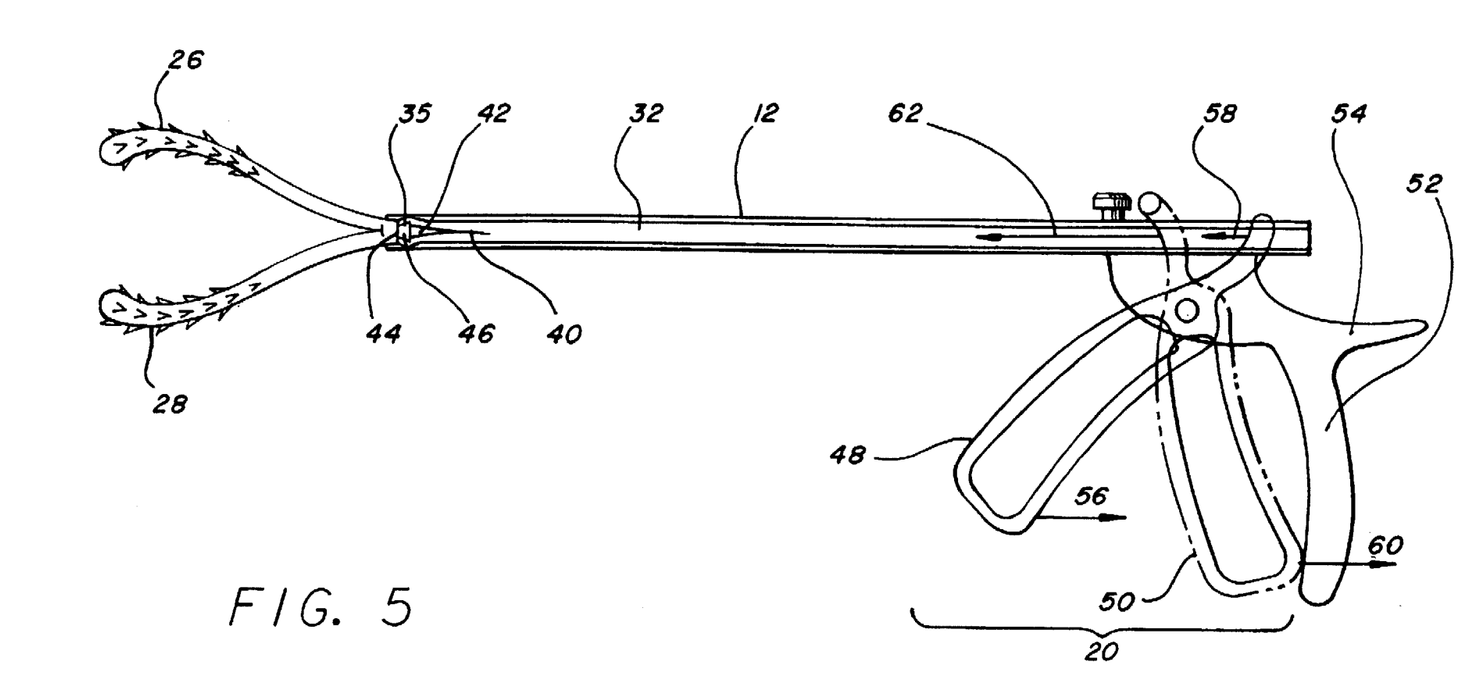
FIG. 5 is a schematic illustrating means for employing the handle member of the micro traumatic tissue manipulator apparatus of the present invention.

FIG. 5 shows a schematic illustrating means for employing the handle member 20 of the manipulator apparatus 10. The first handle lever 48 is attached at or near the proximal end 14 of the shaft 12 while the second handle lever 50 is attached at or near the proximal end 34 of the rod member 32. The stationary member 52 is secured to an outer surface of the shaft 12 such that the shaft 12 may be moved forward in relation to the rod member 32 without affecting the attachment point of the stationary member 52 to the outer surface of the shaft 12. This may be done by way of a slot member located on the outer surface of the shaft 12. When the first handle lever 48 is pulled backwards against the stationary member 52 along line 56, the shaft 12 is pushed forward along line 58 such that the shaft member 12 begins to cover the end 44 of the contact member 18. Continual pressure along line 56 results in covering the jaw members 26 and 28 with the shaft 12. In contrast, when the second handle lever 50 is pulled backwards against the stationary member 52 along line 60, the rod member 32 which is connected to the contact member 18 is pushed outward from the shaft 12 along line 62 such that the contact member 18 extends beyond the distal end 16 of the shaft 12. Accordingly, employment of the first and second handle levers 48 and 50 of the handle member 20 allow for the opening and closing of the jaw members 26 and 28 which comprise the contact member 18.

Figure 6:
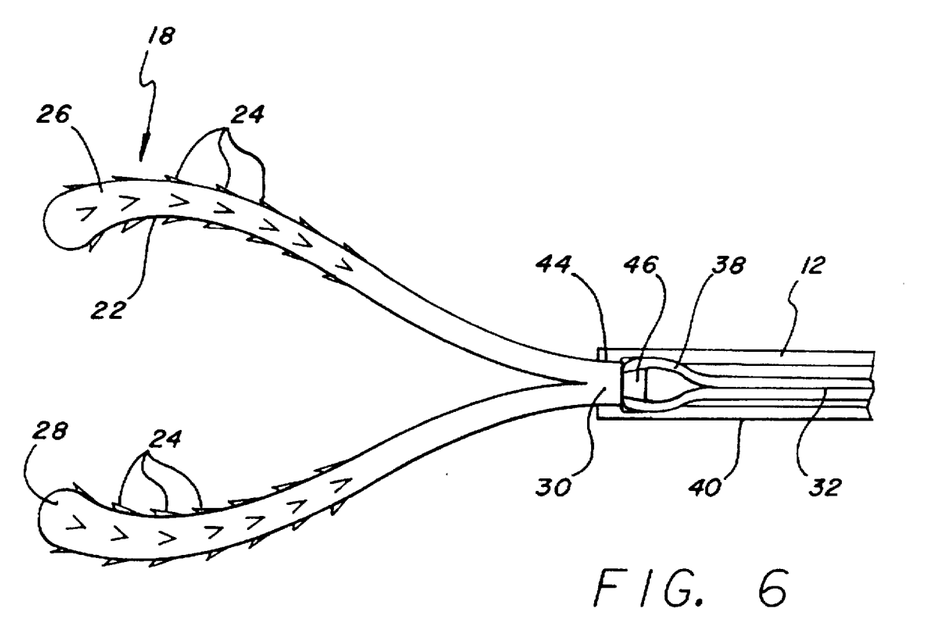
FIG. 6 is an enlarged cross-sectional view of area 6 shown in FIG. 1.

FIG. 6 is an enlarged cross-sectional view of area 6 shown in FIG. 1. The protuberance 46 located at the end 44 of the contact member 18 is secured between the upper and lower members 38 and 40 located at the distal end 36 of the rod member 32 via a snap-type mechanism. The contact member 18 is removable and replaceable with other types of contact members. The pointed projections 24 extending from the tissue contact surface 22 of the contact member 18 are ready to make contact with the targeted tissue in that the jaw members 26 and 28 of the contact member 18 remain open in this position.

Figure 7:
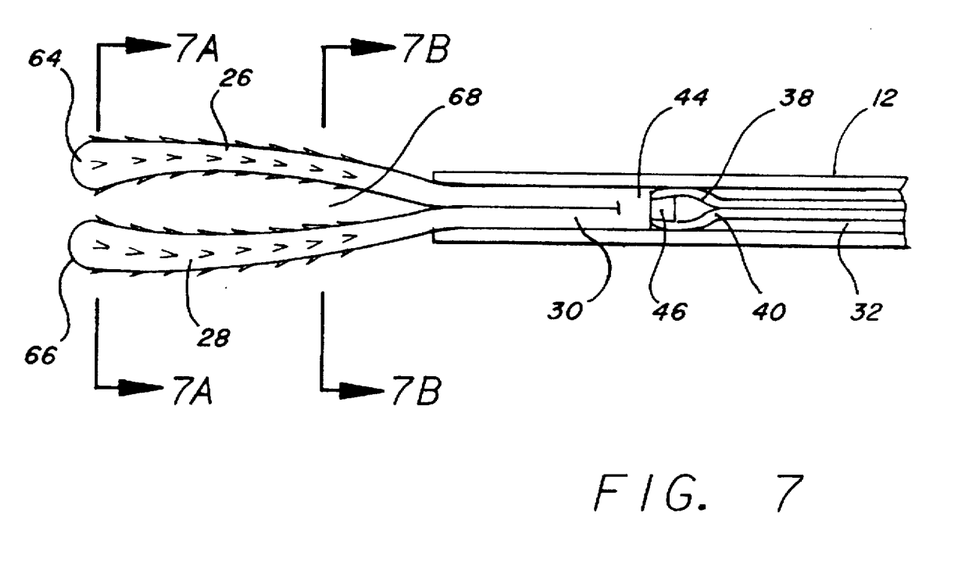
FIG. 7 is an enlarged cross-sectional view of area 7 shown in FIG. 2.
Figure 7A:
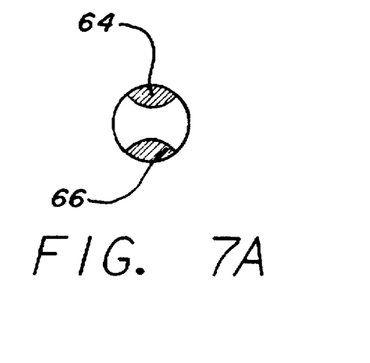
FIG. 7A is a cross-sectional view taken along line A—A of FIG. 7.
Figure 7B:
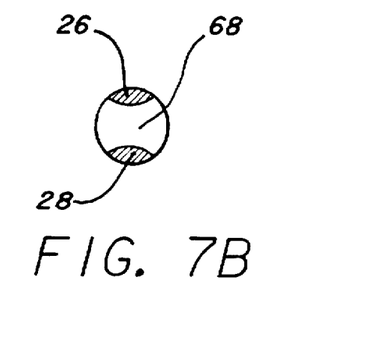
FIG. 7B is a cross-sectional view taken along line B—B of FIG. 7.

FIG. 7 is a cross-sectional view of area 7 shown in FIG. 2. A substantial portion of the contact member 18 is retracted within the shaft 12 thereby enabling any tissue contained between the jaw members 26 and 28 and impaled by the pointed projections 24 to be retained within the contact member 18. The retained tissue may be manipulated and/or held during any surgical procedure without damaging the structural integrity of the tissue. FIG. 7A illustrates that the distal ends 64 and 66 of the jaw members 26 and 28 are maintained in a spaced apart distance from one another even at the most closed position of the contact member 18 (See FIG. 8). FIG. 7B shows the open area 68 between the jaw members 26 and 28 where the targeted tissue is retained.

Figure 8:
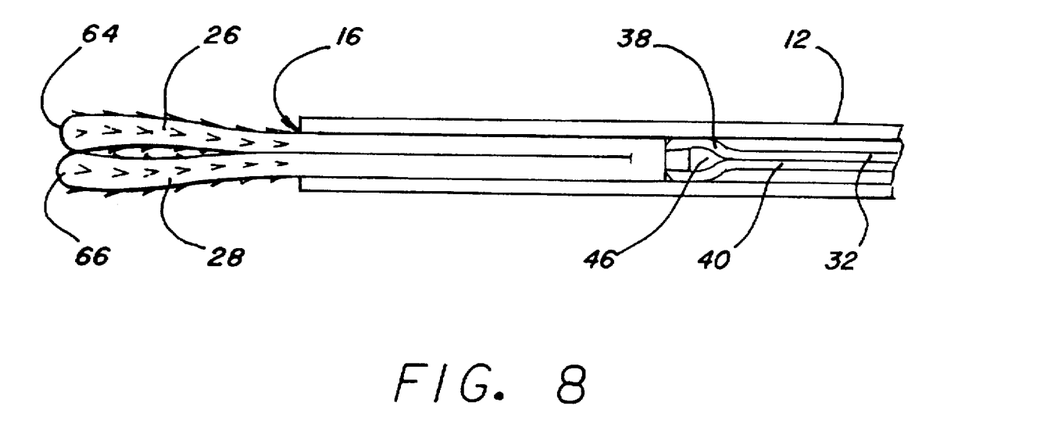
FIG. 8 is an enlarged cross-sectional view of area 8 shown in FIG. 3.

Finally, FIG. 8 shows a cross-sectional view of area 8 shown in FIG. 3 which illustrates the contact member 18 at its most retracted position within the shaft 12. Note that the distal ends 64 and 66 of the jaw members 26 and 28 are maintained in the same spaced apart distance as shown in FIG. 7A.

Figure 9:
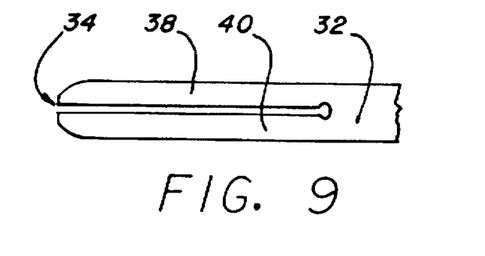
FIG. 9 is a side elevational view of the axial split tube which comprises the attachment means located at the distal end of the rod member.

A side elevational view of the axial split tube which comprises the attachment means located at the distal end 36 of the rod member 32 is shown in FIG. 9. As previously described, the axial split tube comprises upper and lower members 38 and 40.

Figure 10:
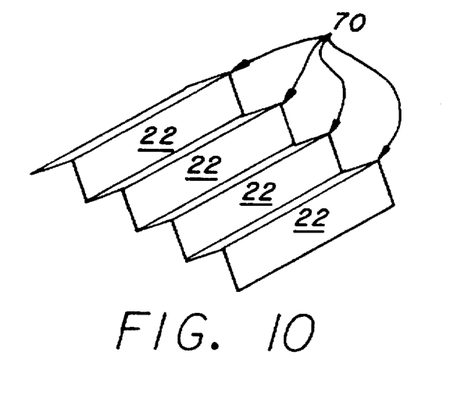
FIGS. 10–13 illustrate a process for constructing the plurality of projections contained on the tissue contact surface of the contact member.
Figure 11:
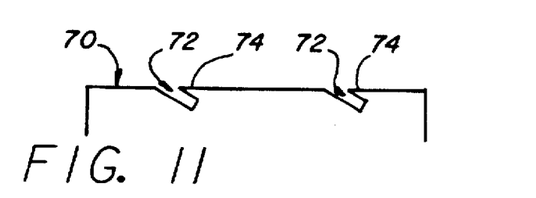
Figure 12:
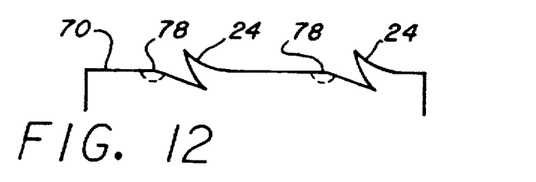
Figure 13:
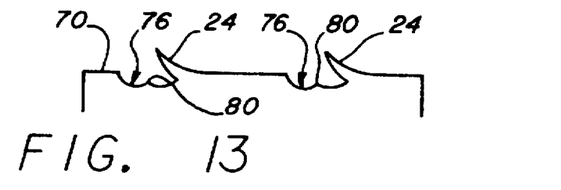

Referring now to FIGS. 10–13, one process for constructing the plurality of pointed projections 24 extending from the tissue contact surface 22 on the contact member 18 is illustrated. FIG. 10 depicts a perspective view of an initial tissue contact surface 22 which is comprised of uniform ridges 70. FIGS. 11–13 depict side elevational views of a single ridge 70. A plurality of angled cuts 72 are made along the length of the top of each ridge 70 as shown in FIG. 11. Next, as shown In FIG. 12, the most pointed ends 74 of the tissue contact surface 22 resulting from the angled cuts 72 are bent upward and away from the direction of the angled cuts 72 such that they form pointed projections 24. Finally, as shown in FIG. 13, a plurality of second cuts 76 may be made to remove the less pointed ends 78 of the tissue contact surface 22 which result from the angled cuts 72 thereby creating a plurality of second lower profile pointed projections 80 located beneath the pointed projections 24.

Figure 14:
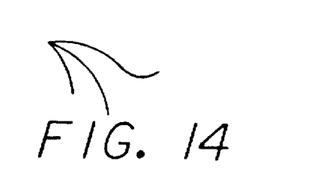
FIG. 14 shows a perspective view of a first preferred embodiment of the projection comprising the plurality of projections contained on the tissue contact surface of the contact member.
Figure 15:
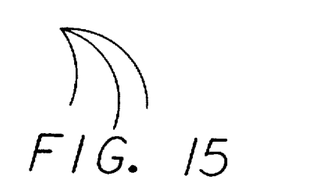
FIG. 15 shows a perspective view of a second preferred embodiment of the projection comprising the plurality of projections contained on the tissue contact surface of the contact member.
Figure 16:
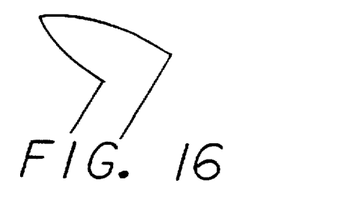
FIG. 16 shows a perspective view of a third preferred embodiment of the projection comprising the plurality of projections contained on the tissue contact surface of the contact member.
Figure 17:
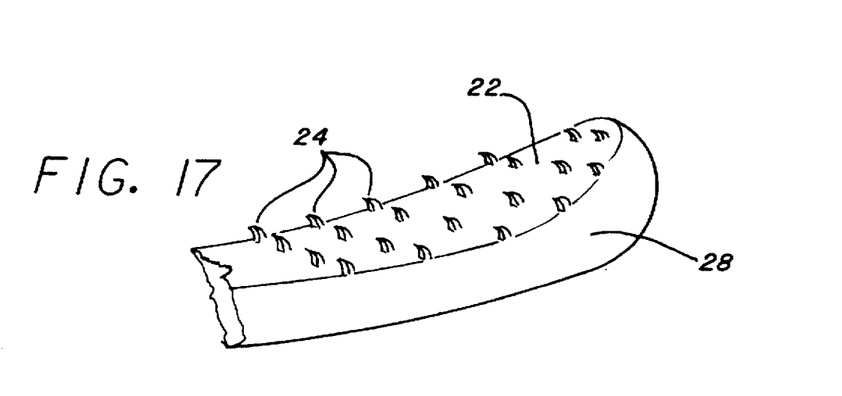
FIG. 17 illustrates a partial jaw member of the contact member showing the plurality of projections extending from the tissue contact surface pointing in the direction of retraction of the targeted tissue.

FIGS. 14 through 16 illustrate alternative embodiments of the pointed projections 24 comprising the plurality of projections extending from the tissue contact surface 22 of the contact member 18. Many other embodiments of the pointed projections 24 may be used in accordance with the present invention provided that the projections are preferably of a sufficient length and geometry to impale the tissue surface without causing structural damage to the tissue. This means that the projections are preferably pointed in the direction of retraction or retrograde of the targeted tissue. The desired direction of the pointed projections 24 is illustrated in FIG. 17 which shows the pointed projections extending from the tissue contact surface 22 of one jaw member 28 which comprises a portion of the contact member 18.

The foregoing is considered as illustrative only of the principles of the invention. Further, since numerous modifications and changes will readily occur to those skilled in the art, it is not desired to limit the invention to an exact construction and operation shown and described. Therefore, all suitable modifications and equivalents fall within the scope of the invention.

I claim:

1. A micro traumatic tissue manipulator apparatus comprising:

an elongated shaft having proximal and distal ends;

a contact member comprising a set of co-acting jaw members wherein each jaw member includes an inner tissue contact surface wherein said contact member is attached near the distal end of said shaft and said tissue contact surface comprises a plurality of at least one of peaked projections and pointed projections with said projections protruding in at least one direction of traction, and wherein each of said co-acting jaw members further comprises a first distal end and a second proximal end, said second proximal ends of said jaw members being connected to one another and said first distal ends maintaining a spaced apart distance from one another in a fully closed position of the co-acting jaw members; and a handle member attached near said proximal end of the shaft.

2. The apparatus of claim 1 wherein said inner tissue contact surface comprises projections protruding toward the distal end of the shaft.

3. The apparatus of claim 1 wherein said contact member is detachable and comprises at least one of a circular shaped pad, a semi-circular shaped pad, an elliptical shaped pad, and a semi-elliptical shaped pad.

4. The apparatus of claim 1 wherein said contact member and said handle member are removable and replaceable.

5. The apparatus of claim 1 further comprising an elongated rod member having proximal and distal ends wherein said rod member is circumferentially contained within said elongated shaft and the distal end of said rod member is attached to the contact member and the proximal end of said rod member is attached to the handle member.

6. The apparatus of claim 5 wherein said contact member further comprises a first end and a second end, said second end comprising a protuberance, and said distal end of said rod member comprises means for retaining said protuberance within said rod member.

7. The apparatus of claim 5 wherein said handle member comprises first and second handle levers which terminate in first and second extension members, respectively, wherein said first extension member is connected to said rod member near its proximal end and said second extension member is connected to said elongated shaft near its proximal end and said first and second handle levers are connected to one another.

8. A micro traumatic tissue manipulator apparatus comprising:

an elongated shaft having proximal and distal ends;

a contact member comprising a set of co-acting jaw members wherein each jaw member includes at least one tissue contact surface having at least one of a continuous semi-circular shape and a continuous semi-elliptical shape, wherein said contact member is attached near said distal end of the shaft and said tissue contact surface comprises a plurality of sharp projections, and wherein each of said co-acting jaw members further comprises a first distal end and a second proximal end, said second proximal ends of said jaw members being connected to one another and said first distal ends maintaining a spaced apart distance from one another in a fully closed position of the co-acting jaw members; and a handle member attached near said proximal end of the shaft.

9. The apparatus of claim 8 wherein said plurality of projections protrude in at least one direction of traction of said tissue.

10. The apparatus of claim 8 wherein said contact member and said handle member are removable.

11. The apparatus of claim 8 wherein said tissue contact surface comprises projections protruding toward the distal end of the shaft.

12. The apparatus of claim 8 further comprising a rod member having proximal and distal ends wherein said rod member is circumferentially contained within said elongated shaft and the distal end of said rod is attached to said contact member and said proximal end of said rod is attached to said handle member.

13. The apparatus of claim 12 wherein said contact member further comprises a first end and a second end, said second end comprising a protuberance, and said proximal end of said rod member comprising an attachment means for attaching said protuberance to the proximal end of said rod member.

14. The apparatus of claim 13 wherein said attachment means comprises an axially split tube having an opening wherein said protuberance is capable of being secured within said opening such that said elongated shaft prevents the opening of said co-acting jaw members unless the distal end of the rod member is sufficiently extended beyond the distal end of the elongated shaft.

15. The apparatus of claim 12 wherein said handle member comprises first and second handle levers which terminate in first and second extension members respectively, wherein said first extension member is connected to said rod member near its proximal end and said second extension member is connected to said elongated shaft near its proximal end and said first and second handle levers are connected to one another.

16. A method of tissue prehension comprising the steps of:

a) contacting the tissue surface with a contact member comprising a set of co-acting jaw members wherein each jaw member includes an inner tissue contact surface having a plurality of sharp projection tips;

b) puncturing the tissue surface with said plurality of sharp projections tips;

c) maintaining a minimal amount of pressure against the projections to maintain contact between the tissue and the projections, while maintaining a spaced-apart distance between the co-acting jaw members at a fully closed position; and d) imparting a torque to the tissue to effect hooking of the tissue on the projections' non cutting base.

* * * * *